United States Patent [19]
Downey, Jr.

[11] Patent Number: 5,587,069
[45] Date of Patent: Dec. 24, 1996

[54] WATER DECONTAMINATION APPARATUS USING PEROXIDE PHOTOLYSIS IONIZER

[76] Inventor: Wayne F. Downey, Jr., 437 Franklin Ct., Collegeville, Pa. 19426

[21] Appl. No.: 480,852

[22] Filed: Jun. 7, 1995

Related U.S. Application Data

[63] Continuation-in-part of Ser. No. 111,988, Aug. 25, 1993, Pat. No. 5,439,595.

[51] Int. Cl.$^6$ .................................................. C02F 1/32
[52] U.S. Cl. ...................... 210/192; 210/199; 210/205; 422/186.12; 422/186.3
[58] Field of Search .......................... 210/748, 758–760, 210/764, 192, 198.1, 202, 205, 199; 422/24, 186.12, 186.3

[56] References Cited

U.S. PATENT DOCUMENTS

| | | | |
|---|---|---|---|
| 1,441,075 | 1/1923 | Fitz | 210/192 |
| 3,523,076 | 8/1970 | Goerz et al. | 210/748 |
| 3,551,091 | 12/1970 | Veloz | 21/102 |
| 3,894,236 | 7/1975 | Hazelrigg | 250/435 |
| 3,920,547 | 11/1975 | Garrison et al. | 210/748 |
| 3,926,556 | 12/1975 | Boucher | 422/21 |
| 4,141,830 | 2/1979 | Last | 210/192 |
| 4,179,616 | 12/1979 | Coviello et al. | 210/177 |
| 4,201,917 | 5/1980 | Graentzel | 250/431 |
| 4,274,970 | 6/1981 | Beitzel | 210/748 |
| 4,535,247 | 8/1985 | Kurtz | 250/436 |
| 4,640,782 | 2/1987 | Burleson | 210/748 |
| 4,818,392 | 4/1989 | Werner et al. | 210/195.3 |
| 4,849,114 | 7/1989 | Zeff et al. | 210/747 |
| 4,857,204 | 8/1989 | Joklik | 210/748 |
| 4,954,147 | 9/1990 | Galgon | 53/53 |
| 4,968,489 | 11/1990 | Peterson | 422/186.3 |
| 5,120,450 | 6/1992 | Stanley, Jr. | 210/748 |
| 5,126,111 | 6/1992 | Al-Ekabi et al. | 422/186.3 |
| 5,131,757 | 7/1992 | Smith | 366/165 |
| 5,174,904 | 12/1992 | Smith | 210/759 |
| 5,266,214 | 11/1993 | Satarzedeh-Amiri | 210/759 |
| 5,266,215 | 11/1993 | Engelhard | 210/748 |
| 5,385,677 | 1/1995 | Venable | 210/748 |
| 5,439,595 | 8/1995 | Downey | 210/748 |

FOREIGN PATENT DOCUMENTS 4000369  7/1991  Germany.

OTHER PUBLICATIONS

Bob Becker, "Analysis of a Second Generation Enhanced Photo–Oxidation Process for the Destruction of Water Born Organic Contaminants", Oct. 1991, pp. 1–15.

Leon M. Dorfman, et al., "Reactivity of Hydroxyl in Radical Aqueous Solutions", 1973, pp. 1–59.

J. Hoigné, et al., "The Role of Hydroxyl Radical Reactions in Ozonization Processes in Aqueous Solutions", 1976, pp. 377–386.

Marugan Malaiyandi, et al., "Removal of Organics in Water Using Hydrogen Peroxide in Presence of Ultraviolet Light", 1980, pp. 1131–1135.

Peroxidation Systems, Inc. "Perox–Pure Organic Destruction Process", undated.

*Primary Examiner*—Peter A. Hruskoci
*Attorney, Agent, or Firm*—Louis M. Heidelberger; Reed Smith Shaw & McClay

[57] ABSTRACT

Apparatus and a method are disclosed for decontaminating water, using an ionizing reactor. Water contaminated by organic compounds is introduced into a chamber in which it is concurrently irradiated by microwave and an ultraviolet source to activate it by photolysis. The water is then introduced to a hydroxyl reactor chamber. An oxidizing reagent, such as hydrogen peroxide, is irradiated by subjecting it to the UV source. The activated water and irradiated oxidizing reagent are then vectored to a locus at which they are mixed under continuing UV radiation from the source. The apparatus and method may be incorporated into a water treatment system employing existing contaminant extraction techniques, such as immiscible fluids separation and turbo-aspirated sparging.

18 Claims, 6 Drawing Sheets

WATER DECONTAMINATION APPARATUS USING PEROXIDE PHOTOLYSIS IONIZER

CROSS-REFERENCE TO RELATED APPLICATION

This application is a continuation-in-part of application Ser. No. 08/111,988, filed Aug. 25, 1993, now U.S. Pat. No. 5,439,595.

BACKGROUND OF THE INVENTION

This invention relates to a water treatment method and an apparatus, and more particularly, to a method and apparatus for the removal from aqueous fluid of toxic and potentially hazardous organic compounds. The present method and apparatus exploit, synergistically, ultraviolet photolysis, the use of hydroxyl radicals, and microwave energy to, optimize the oxidation of organic contaminants in water.

The use of ultraviolet light and oxidants, such as ozone and hydrogen peroxide, to produce hydroxyl radicals, is well-known. Such a technique has been used to enhance oxidation of organic contaminants in industrial waste water, groundwater and other aqueous solutions. Direct photolysis of organic compounds by intense ultraviolet light is also well known and is used extensively in the biocidal water treatment industry. Microwave radiation (electromagnetic waves having a wavelength between about 0.3 and 30 centimeters) is commonly used to induce rapid heating of materials from within by oscillatory stimulation of hydrogen and nitrogen atoms within water and organic molecules. Oxidation of organic contaminants by ultraviolet light or by chemical reaction with hydrogen peroxide ultimately yields innocuous products: carbon dioxide, elemental carbon, water and oxygen.

It has now been found that exploitation of the above techniques in a single compact apparatus creates a potent oxidative water treatment method.

Existing apparatus and methods, using ultraviolet (UV) light and reagents such as hydrogen peroxide to create hydroxyl radicals, are able to treat substantial volumes of water, on the order of hundreds of gallons per minute. In "first generation" systems of this sort, it was proposed that low pressure UV discharge lamps be encased in quartz tubes immersed in tanks of water to be treated. Hydrogen peroxide was added to the water, and the mixture was allowed to flow around the submerged lamps. Problems with rapid fouling of the lamps and low production of hydroxyl radicals in such devices soon became apparent. Second generation apparatus of the above type incorporated manual cleaning mechanisms, and the use of polymer coatings (such as "Teflon" PTFE) on the quartz sleeve, additional oxidizers (such as ozone), and catalyzing additives (such as $TiO_2$) to enhance the rate of radical production. Lasers also have been used in efforts to increase energy transfer efficiency. Some efforts were successful to some extent, but at the price of significantly greater complexity and cost.

In known prior art apparatus and methods, the oxidizing reagent is added to the water prior to exposure of the mixture to the UV radiation. Since chemical oxidation is rapid, in such arrangements inorganic precipitates quickly form on the quartz sleeve or window surfaces, resulting in immediate and cumulative attenuation of the UV radiation.

Moreover, in known prior art apparatus and methods, addition of the oxidizing reagent to the water prior to UV exposure results in dilution of the reagent, so that the photon density of the UV radiation reaching the oxidant molecules is reduced by preferential absorption by the water, scattering and absorption by entrained particles in the water, and absorption by solutes. Sluggish mixing of the solution during irradiation also minimizes contact of the few radicals that are produced close to the light source, resulting in a relatively inefficient and certainly less than optimal capability for contaminant destruction.

The present invention provides a method and apparatus which addresses and obviates the above shortcomings of the prior art, by synergistically enhancing contaminant destruction by complementary techniques.

SUMMARY OF THE INVENTION

In one of its aspects, the present invention provides, for use in the treatment of waste water, an ionizing reactor for photochemically oxidizing organic compounds in aqueous solutions, using microwave-assisted photolysis and hydroxyl radical oxidation. The photolysis, production of hydroxyl radicals and the final hydroxylation reaction are all effected using a high pressure UV short arc lamp. Peroxide activation is made to take place in such a manner that a pure reagent is irradiated immediately prior to water contact, thus maximizing $O_3$ and $HO_2^+$ and $OH^+$ radical production. The reagent is injected into a downstream hydroxylation chamber, where it is activated and mixed in a reaction zone with the pre-sensitized water, still under irradiation. The mixing is made to take place at a paraxial focus, where the ionization kinetics are most aggressive and the principal oxidative destruction of organic compounds occurs. The activated oxidizing reagent, containing free radicals, and the microwave and photosensitized water, are thus mixed vigorously at a point where incident concentrated deep UV radiation irradiates both fluids at once, to enhance the chemical degradation reaction.

Thus, a principal feature of a preferred embodiment of the invention is the simultaneous activation of pure oxidizing reagent with direct UV light and secondary photolysis and sensitization of contaminated water with UV radiation emitted from the wall of a tube (preferably of quartz) and with microwave radiation from a microwave source (magnetron) positioned to direct high energy electromagnetic waves into the angular path of influent water circulating in a vortex around the tube.

In its method aspect, the invention contemplates the use of a concentrated beam of deep spectrum ultraviolet light, which is manipulated using an optical array to simultaneously irradiate a reagent such as hydrogen peroxide and to irradiate out of fluid contact with the reagent (and preferably in an environment charged with microwave radiation) water to be treated. The water and the reagent are then mixed vigorously, under continued UV irradiation to optimize oxidation of water-borne contaminants.

A prime advantage of the above-described peroxide photolysis ionizer is that a maximum number of free radicals are produced using one UV source, which is itself safely and efficiently located separate from the reaction chamber. Pre-sensitization of the water by photolysis enhances the ultimate reaction of the contaminants with the free radicals during subsequent hydroxylation.

Because the hydroxylation reaction occurs downstream from any light transmitting or reflecting surfaces, it does not contribute to precipitate fouling of those surfaces, a common problem in the prior art.

As indicated above, all of the fluid to be treated is preferably made to converge at a narrow vertex where a concentrated beam of UV light of optimal wavelength is directed. This minimizes the energy needed to generate free radicals while maximizing the treatment volume capability of the apparatus.

The present invention may be used to good advantage as part of a comprehensive water treatment system in an industrial setting requiring the removal and rapid destruction of recalcitrant contaminants from water, within a minimal space. In one of its embodiments, the present invention may be incorporated into a system comprising a coalescing separator for receiving waste water, a multi-stage turbo-aspiration unit, and one or more peroxide photolysis ionizers of the above-described type associated with the various stages of the turbo-aspiration unit. All of the above components, it has been found, can be mounted on the chassis of a small truck or trailer for portability.

BRIEF DESCRIPTION OF THE DRAWINGS

There are seen in the drawings forms of the invention which are presently preferred (and which constitute the best mode contemplated for carrying the invention into effect), but it should be understood that the invention is not limited to the precise arrangements and instrumentalities shown.

DETAILED DESCRIPTION OF THE INVENTION

Figure 1:
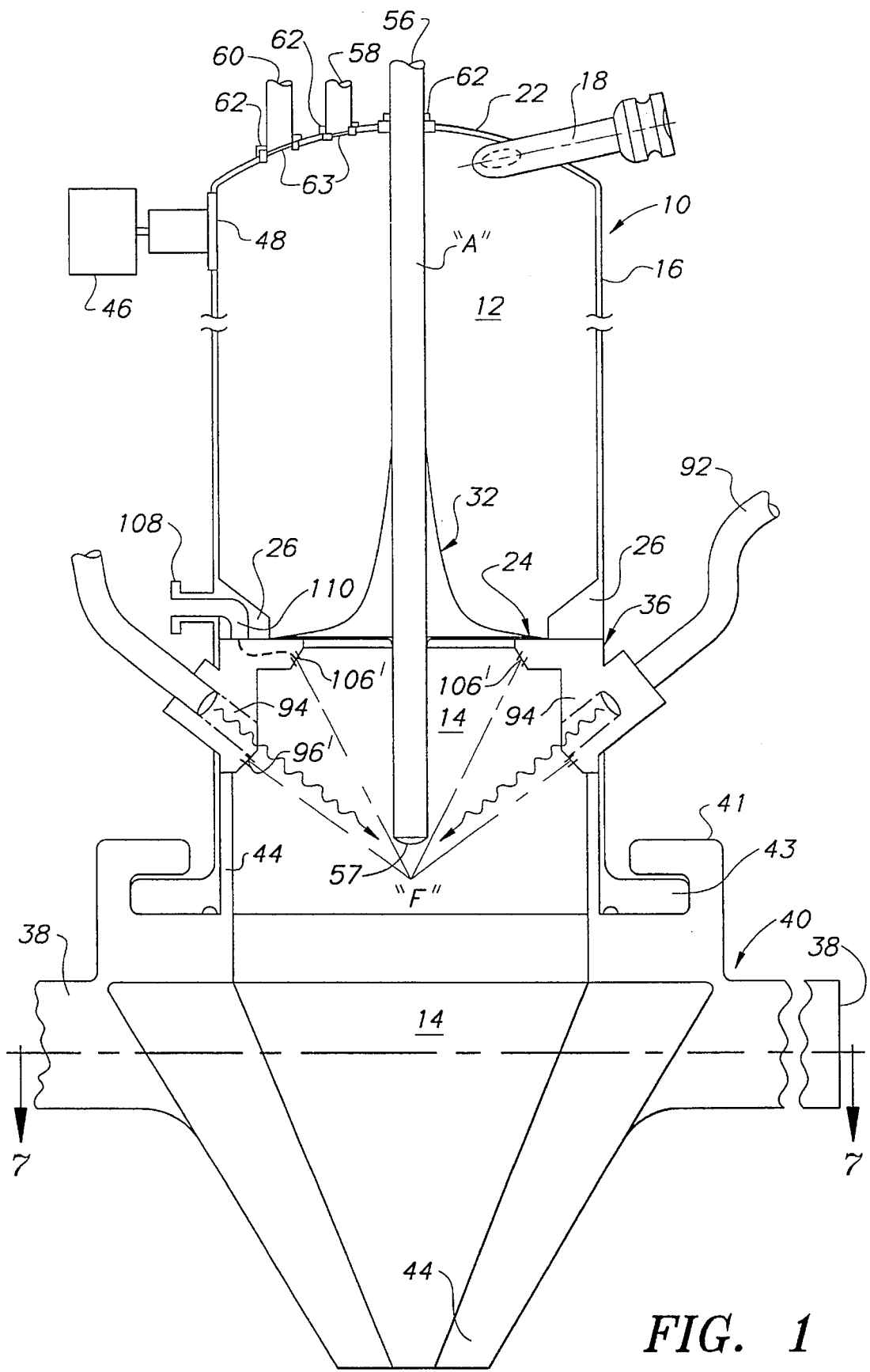
FIG. 1 is a side elevation view, in cross section, of a chamber assembly of the peroxide photolysis ionizer of the present invention.

Referring now to the drawings in detail, wherein like elements are designated by like reference numerals, there is seen in FIG. 1 an-ionizing reactor, designated generally by the reference numeral 10. The reactor 10 comprises, in general, a photolysis chamber assembly, designated generally by the reference numeral 12, and a hydroxyl reactor chamber, designated generally by the reference numeral 14.

Figure 5:
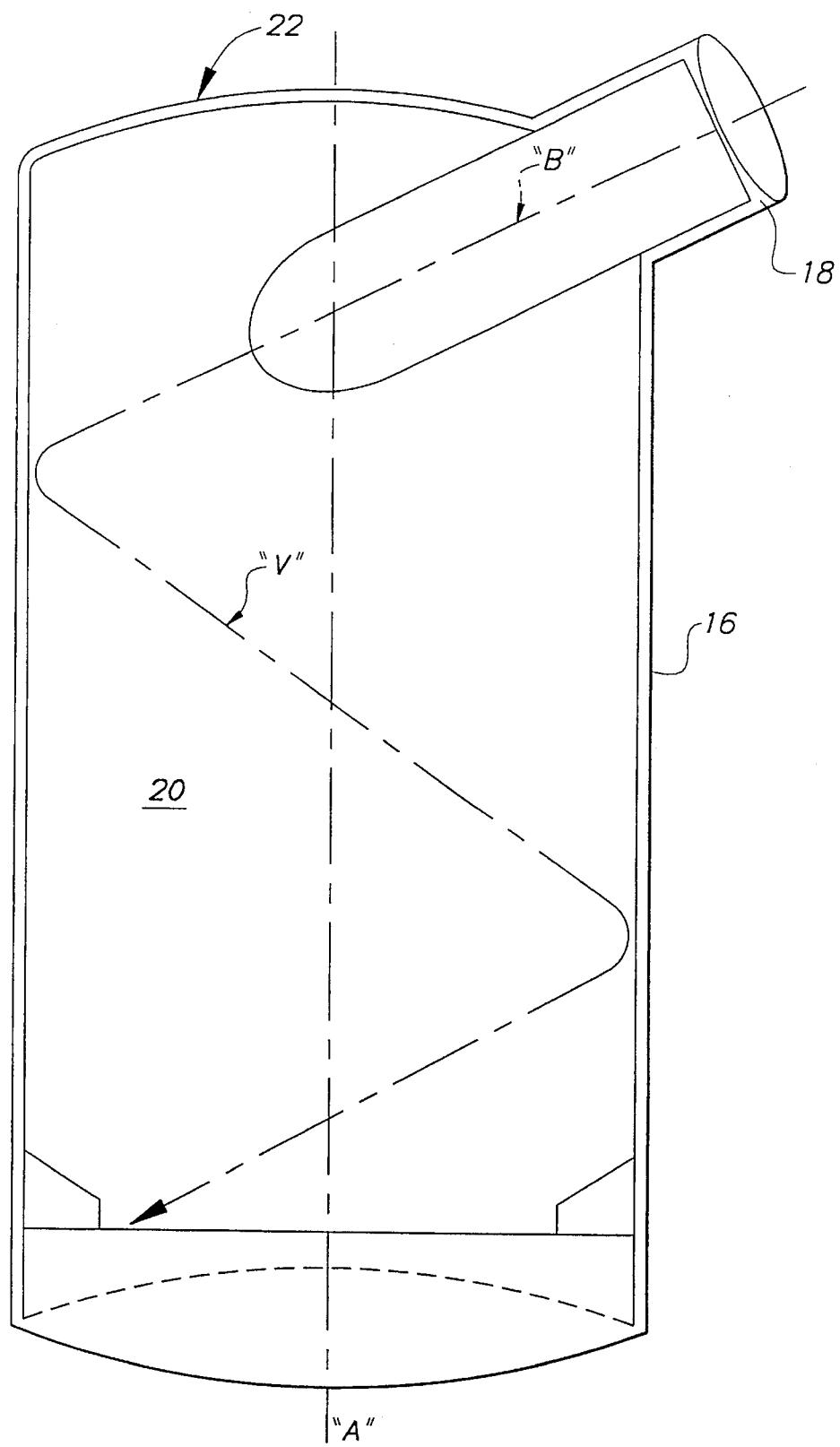
FIG. 5 is a side elevation view of a photolysis chamber in accordance with the invention.
Figure 6:
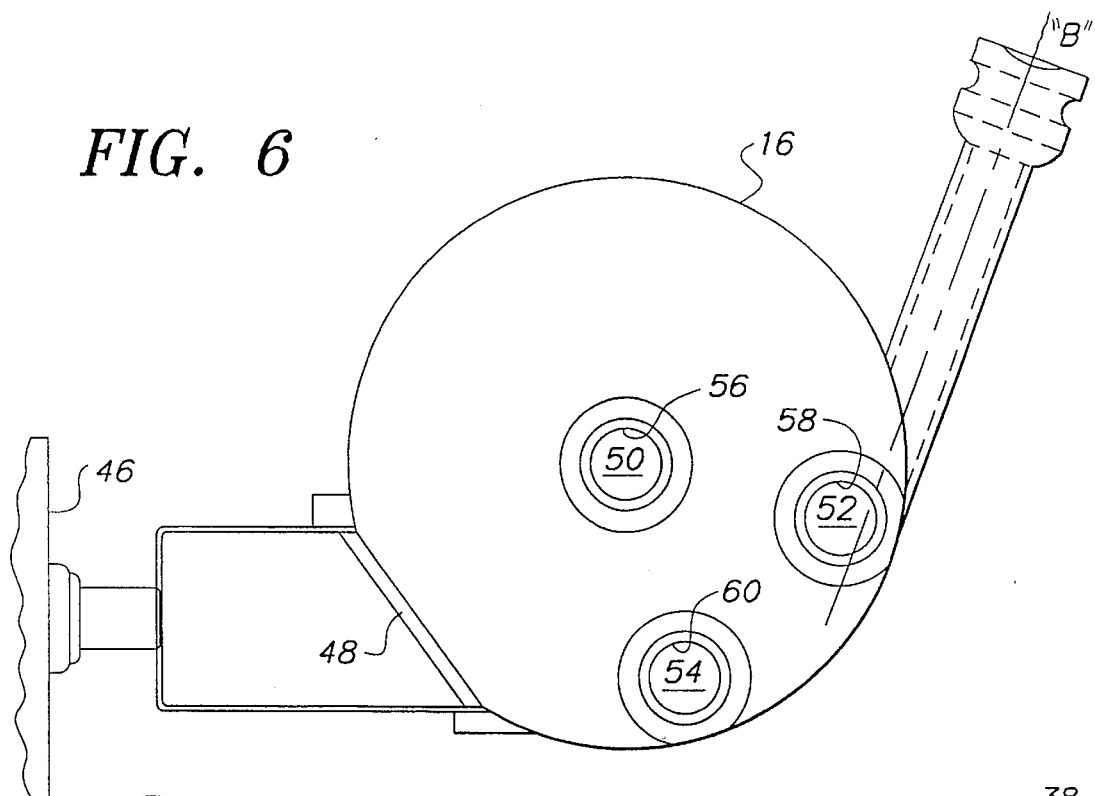
FIG. 6 is a top view of a photolysis chamber in accordance with the invention.

Referring now to FIGS. 5 and 6 in addition to FIG. 1, the photolysis chamber assembly 12 consists, in the illustrated embodiment, of a generally elongated cylindrical shell 16, preferably of stainless steel. Associated with the shell 16 is a water injection port 18. As is perhaps best seen in FIGS. 5 and 6, the port 18 is so arranged and oriented with respect to the longitudinal axis "A" of the shell 16 that a stream of water flowing through the port 18 will impinge on the curved interior wall 20 of the shell 16 and assume a helical or volute path, shown and designated diagrammatically in FIG. 5 as "V". Referring now to FIG. 6, it will be seen that in a transverse cross-sectional view, the port 18 enters tangentially with respect to the circular cross-section of the shell 16. Referring again to FIG. 5, it will be seen that the longitudinal axis "B" of the water port 18 is oblique with respect to the axis "A" of the shell 16, thus encouraging development of the desired helical or volute flow of water within the shell 16.

Figure 7:
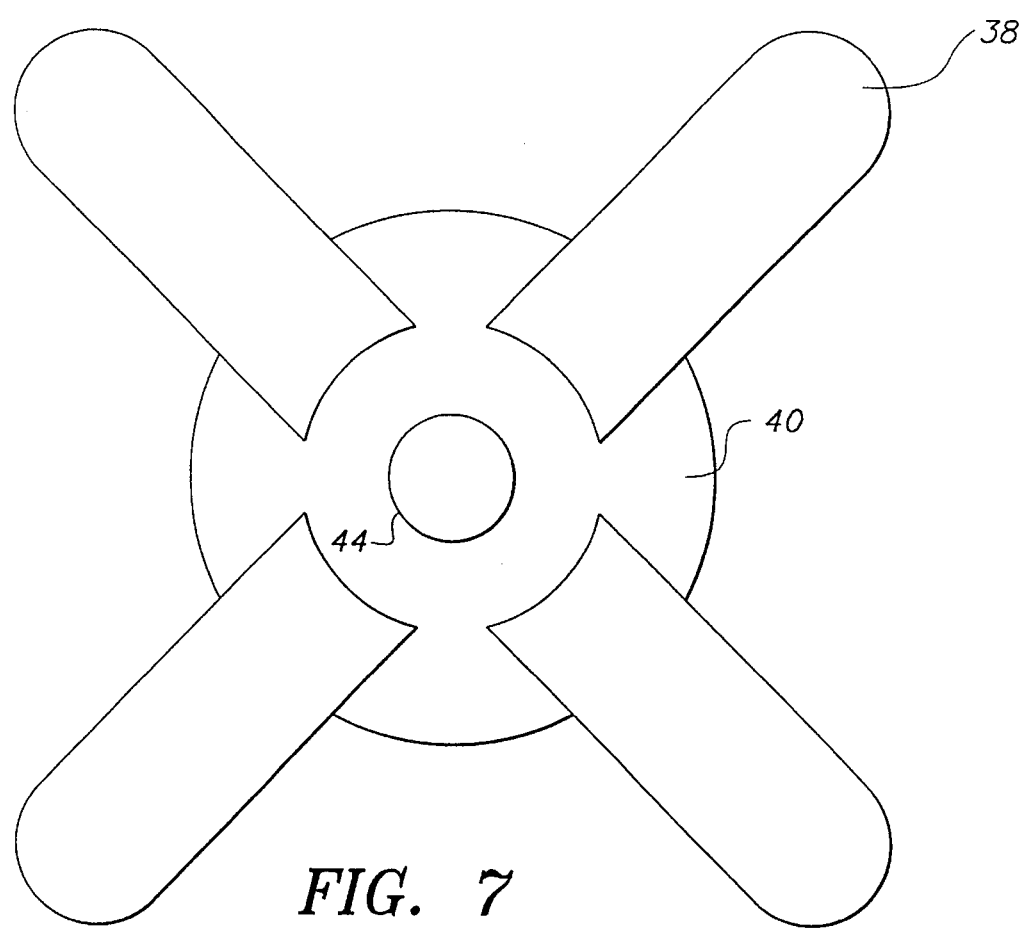
FIG. 7 is an end view, in cross-section, taken along the line 7—7 in FIG. 1.

Referring again to FIG. 1 and also to FIG. 6, the shell 16 is capped at one end by a curved influent endcap 22, which supports the water injection port 18 and provides tube ports 50, 52 and 54. Referring to FIG. 1, the other end of the shell 16 is capped with a conical effluent mixing endcap designated generally by the reference numeral 40, which is secured to the shell 16 by a camlock bezel 41. Access may be had to the hydroxyl chamber 14 and photolysis chamber 12 upon removal of the endcap 40. This can be accomplished, in the illustrated embodiment, by a ¼ rotation twist of the camlock bezel 41, manually, using the handles 38 best seen in FIG. 7. A suitable "O" ring 42 is disposed between the endcap 40 and a camlock flange 43 disposed on the shell 16.

Referring again to FIG. 1, associated with the shell 16 is a ringjet flange, designated generally by the reference numeral 24. The ringjet flange 24 is disposed within the shell 16 when the photolysis chamber assembly 12 is assembled, and includes a hyperbolic reflector body 32, with a quadratic surface, shaped to direct radiation within the shell 16 for maximum effect. The reflector body 32 is preferably fabricated of highly polished aluminum, sputter-coated with sapphire to provide abrasion and corrosion protection and to optimize spectral reflectivity. Bolts 34, seen in FIG. 4, secure the reflector 32 to the ringjet flange 24.

Associated with the ringjet flange 24 is a water jet control manifold 36 (seen in detail in FIG. 3 and 4 and described below).

The ringjet flange 24 seats on a retainer flange 26 (FIG. 1), which is part of the shell 16, and serves to support the assembly made up of the ringjet flange 24 and the reflector body 32. The ringjet flange 24 and retainer flange 26 partition the photolysis chamber 12 from the hydroxylation chamber 14. A lip 44, projecting from the conical endcap 40 (FIG. 1) seats on the ringjet flange 24 to hold the flange in place when the conical endcap 40 is locked in place.

Other aspects of the ionizing reactor 10 will now be described in detail.

Referring now to FIG. 6, associated with the shell 16, at a position generally juxtaposed to the water port 18, is a magnetron 46. The magnetron 46 is associated with a microwave-transparent "window" 48 in the shell 16, which enables microwave radiation produced by the magnetron 46 to enter the shell 16 and impinge upon water entering the shell 16 through the port 18. A suitable cooling fan, not shown, or other suitable cooling arrangement, may be provided for the magnetron.

Associated with the above-mentioned ports 50, 52 and 54 of the endcap 22 are quartz tubes 56, 58 and 60. Jam nuts 62, with suitable gasket features, secure the quartz tubes 56, 58 and 60 to the endcap 22 at the respective ports 50–54.

The quartz tubes 56–60, it should be understood, are evacuated and sealed, and serve as optical light pipes. They extend directly from a light concentrating condenser 81 at the light source (to be described below) to the reactor 10. In the illustrated embodiment the quartz tube 56 traverses the length of the photolysis chamber 12 in a direction parallel to the axis "A," and passes through the hyperbolic reflector body 32 and ringjet flange 24 into the hydroxyl reactor chamber 14.

Referring again to FIG. 1, the terminal ends of the quartz tubes 58 and 60 are sealed by quartz plano-concave lenses 63, and the terminal end of the tube 56 is sealed by a quartz plano-convex lens 57. The tubes are evacuated and made to retain vacuum to optimize transmission of UV light. The ports 52 and 54 and the quartz tubes 58 and 60, it should be understood, are positioned and arranged so that UV light conducted by the quartz tubes 58 and 60 irradiates water as it enters the photolysis chamber 12 along path "B" as shown in FIG. 6. Also, spurious UV light is diffused throughout the photolysis chamber 12 by Lambertian diffusion from the wall of the tube 56.

Figure 2:
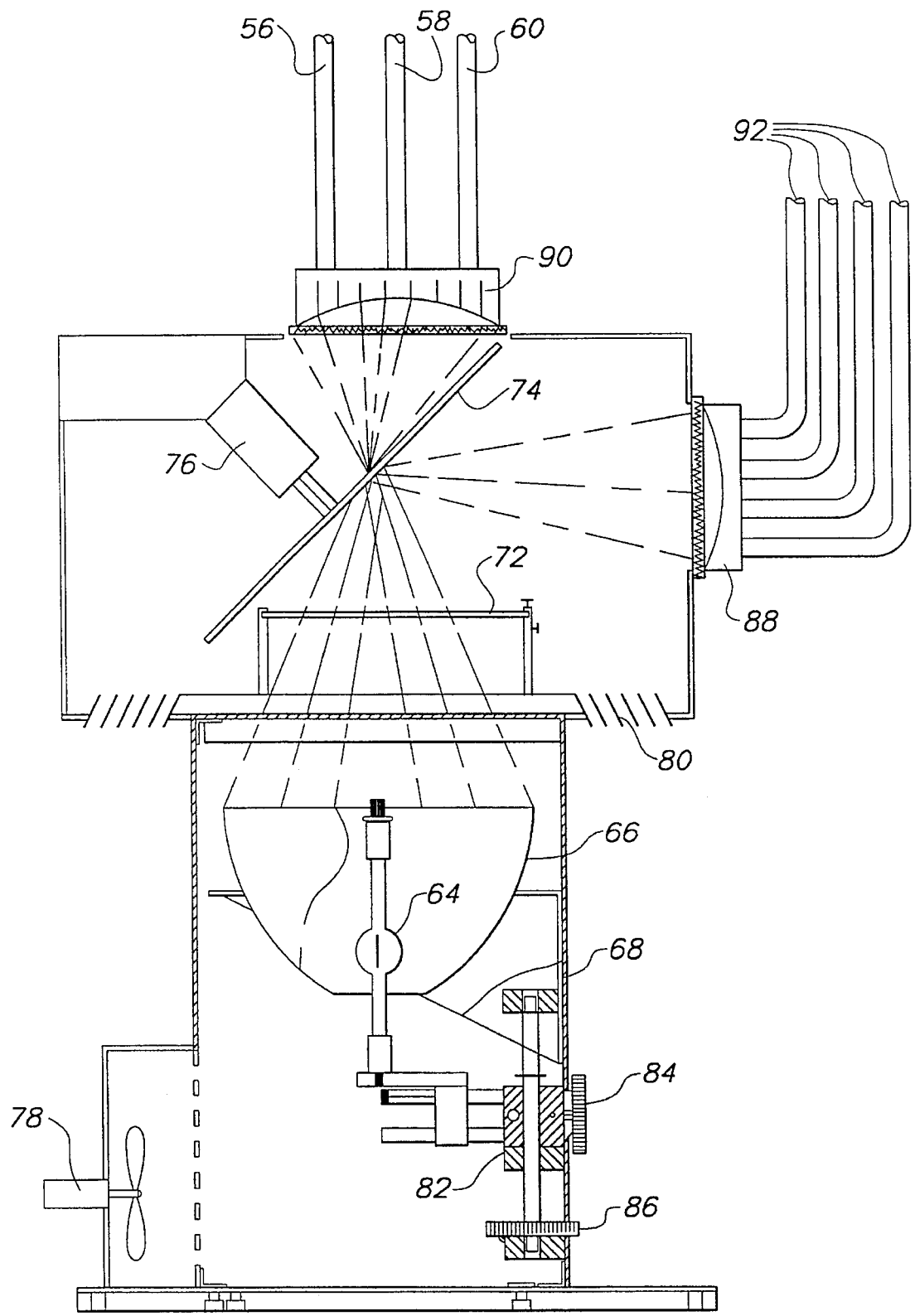
FIG. 2 is a front elevation view, in cross section, of an arc lamp and exemplary associated fiber optic transmission bundles and quartz tubes for use in the present invention.

Referring now to FIG. 2, an exemplary ultraviolet light source is seen. The illustrated source provides an arc lamp 64, disposed within an ellipsoidal reflector 66, both within a housing 68. A cross-slide mechanism 82, associated with the housing 68 and arc lamp 64, provides for focus and alignment adjustments for the arc lamp. Any suitable mechanism may be used for incremental adjustment of the position of the arc lamp 64. Suitable adjustment wheels or knobs 84 (for arc lamp alignment) and 86 (for focus) are provided. The arc lamp 64 may be a 350 to 1000 watt high pressure snort arc mercury-xenon lamp, of the kind presently commercially available from Advanced Radiation Corp., Ushio Corp. and Ultra Violet Products, among others.

Referring again to FIG. 2, a quadfurcated fiber optic collector 88 is juxtaposed to the elliptical reflector 66 at a 90° angle from the beam splitting chopper 74. Approximately fifty percent (50%) of the UV light passes directly through the chopper 74 and is focused into the quartz tubes 56, 58 and 60 (or light conducting elements associated with them) by a condenser 90. The other approximately fifty percent (50%) of reflected UV light is collected and collimated by the fiber optic collector 88 and directed through separate fiber optic bundles 92 (four in the illustrated embodiment) to the hydroxyl reaction chamber 14. In the chamber 14, each of the bundles terminates in a sealed sapphire lens housing 94, best seen in FIG. 1. The lens housings 94 oppose each other at 90° angles, but their optical axes are preferably angled about 40 degrees (40°) with respect to the longitudinal axis "A" of the shell 16, to intersect at a paraxial focal zone.

The application of UV radiation to the fiber optic bundles 92 and the quartz tubes 56, 58 and 60 in the above manner results in irradiation of the above-mentioned paraxial focal zone in the hydroxyl reaction chamber 14, and, by incident impingement and Lambertian diffusion, irradiation of the photolysis chamber 12. The photolysis chamber 12 is preferably also simultaneously subjected to microwave radiation produced by the magnetron 46 (as described above), so that water in the photolysis chamber 12 is both irradiated and sensitized by the concurrent microwave and UV photon impingement.

Figure 4:
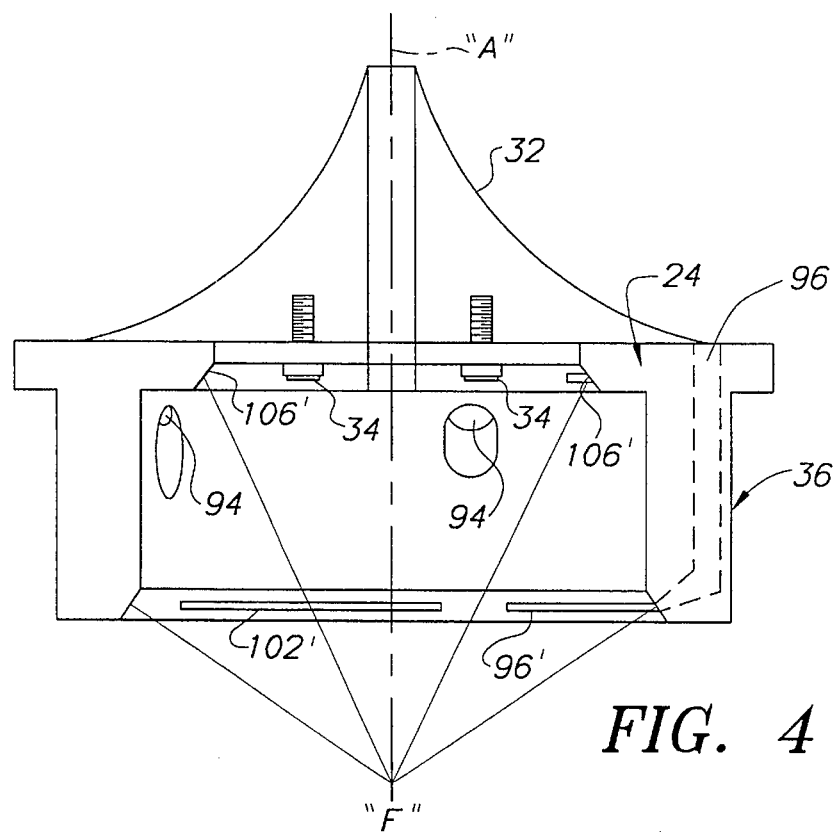
FIG. 4 is a cross-sectional view of the ringjet water and reagent flow control flange shown in FIG. 3, taken along the line 4—4 in FIG. 3.
Figure 3:
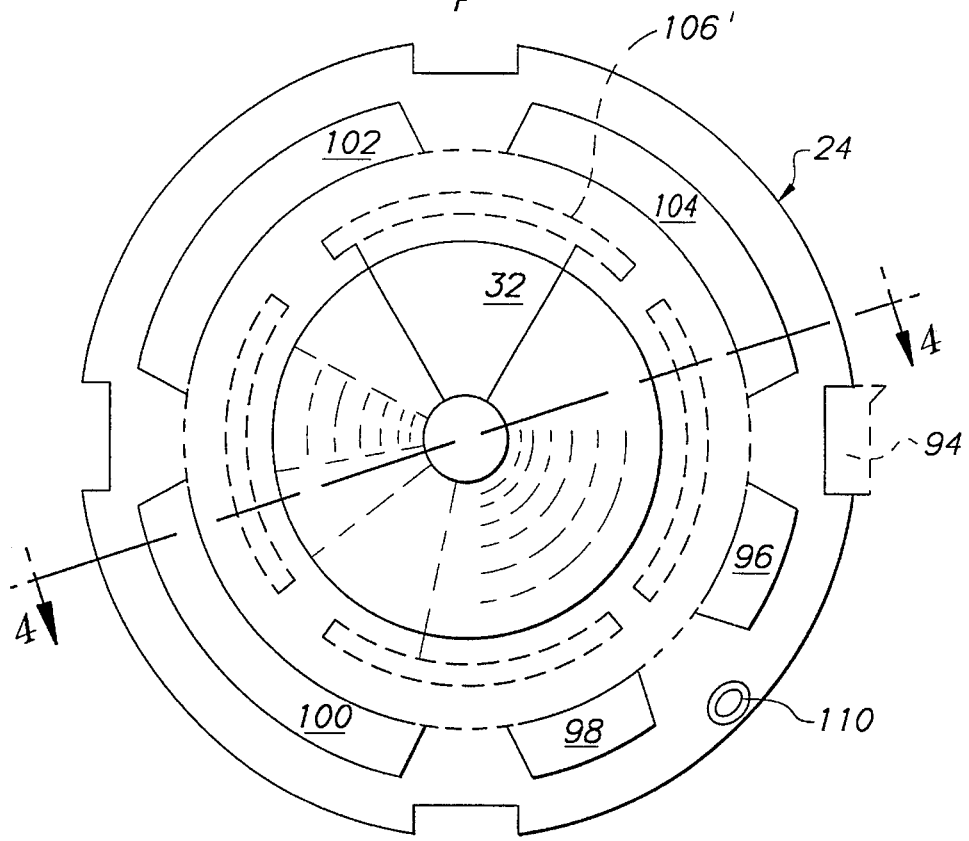
FIG. 3 is a top plan view of a ringjet water and reagent flow control flange used in the invention.

Referring now to FIGS. 1, 3 and 4, the manner in which activated reagent and sensitized water are directed to a paraxial focal zone in the hydroxyl reactor chamber 14 (where UV radiation also impinges on both fluids) will now be described. It is intended that the principal oxidation reaction produced by the reactor 10 occur at this locus, and oxidation may be further enhanced by high shear mixing in a downstream turbo-aspirated sparging apparatus, as will be described below.

Referring now to FIGS. 1, 3 and 4, the ringjet flange 24 will be described in greater detail.

Referring to FIGS. 3 and 4, the ringjet flange 24 is provided with and pierced by a circular array of arcuate water passages 96, 98, 100, 102 and 104, terminating in orifices 96'–104' (five in the illustrated embodiment). The passages 96–104 extend through the ringjet flange 24 at a preferred angle of about 20° with respect to the longitudinal axis "A" of the hydroxyl reactor chamber 14. The illustrated passages 96–104 and orifices 96'–104' are distributed around the periphery of the ringjet flange 24 at the same radial distance from its center. As is seen in FIG. 4, the respective longitudinal center lines "L" of the orifices 96'–104' converge at a locus (or focal zone), here designated "F". The oxidizing reagent, hydrogen peroxide, is introduced into the hydroxyl reactor chamber 14 through a passage 106 and a circular array of arcuate slit-like orifices 106' (such as, for example, weir plates), seen in dotted line in FIG. 3. Other specific configurations for the orifices 106' will occur to those skilled in the art. The orifices 106' are preferably disposed concentrically within the circular array of the water passages 96–104, and are angled with respect to the axis "A" to direct reagent toward the focus, or focal zone, "F. " The reagent may be introduced to the reactor 10 under pressure, through ports such as the port 108 seen in FIG. 1, The port 108 is in communication with a passage 110 through the retainer flange 26. The passage 110 aligns and communicates with the passage 106, best seen in FIG. 3, and the passage 106 communicates with the orifices 106'. The orifices 106' are so positioned and arranged that reagent emerging from the orifices 106' does so at an angle with respect to the longitudinal axis "A" of the hydroxyl reactor chamber 14. Such a configuration produces the cone of reagent within or closely associated with the cone of water impinging at the same locus "F. " The UV light from the fiber optic bundles 92 and quartz tube 56 is also directed to the focal zone at the locus "F. " Thus, is will be seen that the oxidizing reagent (hydrogen peroxide) emerging from the orifices 106' into a zone adjacent the locus or focal zone "F" is activated by the incident UV light. The oxidizing reagent containing free radicals, and the microwaved and photosensitized water, are vigorously mixed, and incident concentrated radiation continues to irradiate both fluids as contact mixing takes place in the focal zone "F. "

Figure 8:
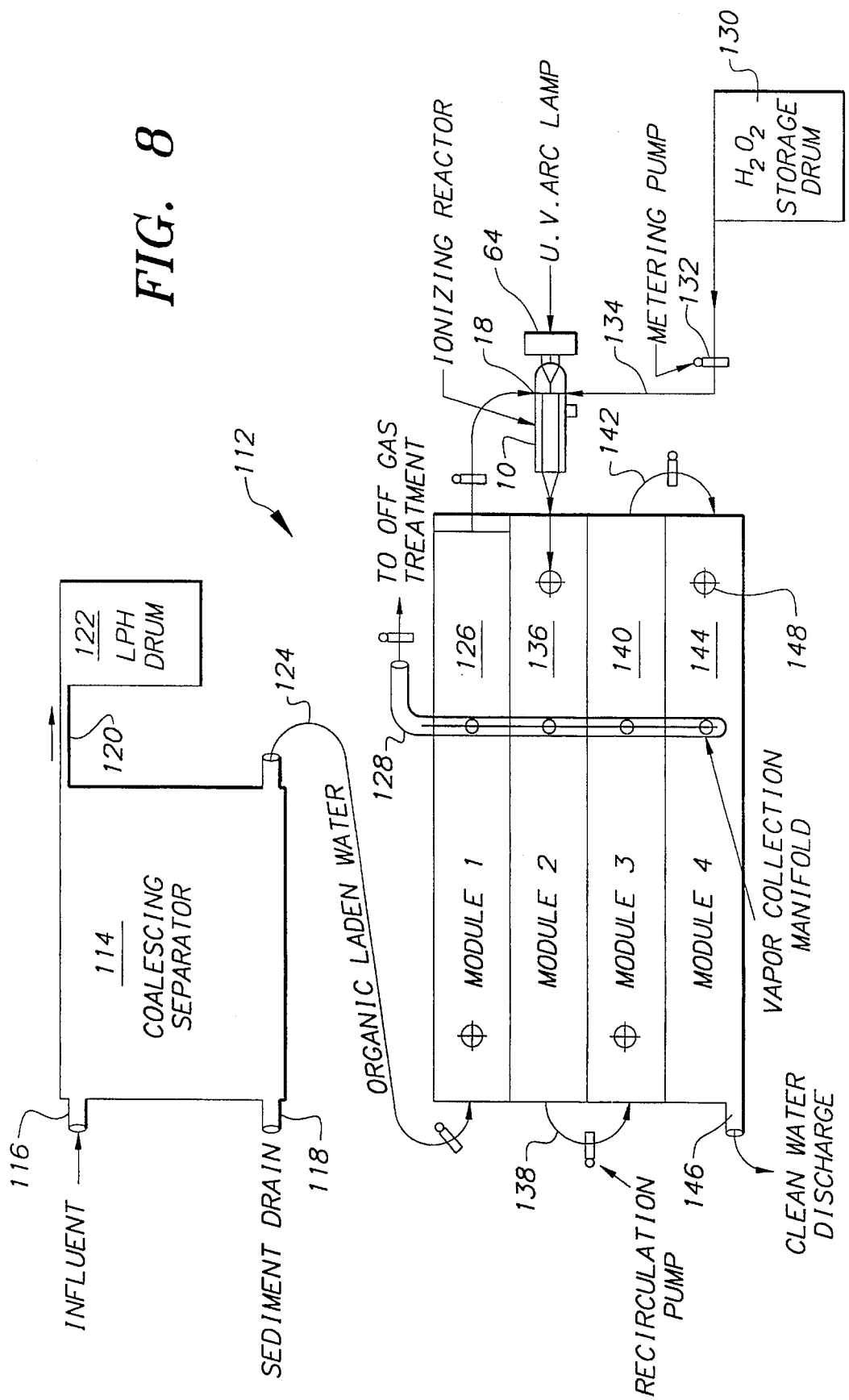
FIG. 8 is a flow diagram of a water treatment system in accordance with the invention.

FIG. 8 illustrates a water treatment system in accordance with the invention, in which the above-described ionizing reactor 10 cooperates with a number of known components assembled in a unique manner, to provide efficient treatment of contaminated water. Referring now to FIG. 8, the system, designated generally by the reference numeral 112, includes a coalescing separator 114, into which influent is introduced at 116. Heavy sediments and immiscible fluids are mechanically separated from the influent and removed at the sediment drain 118. Lighter contaminants, such as floating hydrocarbons in the liquid phase, are drawn off at a conduit 120 to a collection and storage drum 122. The remaining water, still containing dissolved organic contaminants, is withdrawn from the separator 114 through the conduit 124, and pumped as input into a module containing a turbo-aspirated sparger 126. Off gas from the sparger is removed through a manifold 128, and the water output of the sparger is directed and pumped to the water injection port 18 of an ionizing reactor 10. Oxidizing reagent, such as hydrogen peroxide, is provided to the reactor 10 from a storage drum 130, by means of a metering pump 132 and conduit 134.

The effluent from the ionizing reactor 10 is introduced into a second sparger 136, whose off gasses are drawn off into the manifold 128. The efflux from the sparger 136 is pumped through a conduit 138 to a third sparger 140 (also associated with the manifold 128), and from the third sparger 140 through a conduit 142 to a fourth sparger 144

(also associated with the manifold 128). Clean water is discharged from the fourth sparger 144 at a conduit 146. A turbo-aspirator 148 may advantageously be associated with each module containing a sparger 126, 136, 140 and 144.

It will be appreciated that, although four spargers (and thus four sparging stages) are shown, the present invention may be used with other numbers of sparging stages. Various commercially available sparging units are suitable for use in the above-described system.

The present invention may be embodied in other specific forms without departing from its spirit or essential attributes. Accordingly, reference should be made to the appended claims, rather than the foregoing specification, as indicating the scope of the invention.

I claim:

1. For use in the treatment of water, apparatus comprising a first chamber, a water inlet port in fluid communication with said first chamber, a second chamber in fluid communication with said first chamber and having an outlet port, first orifice means in fluid communication with said second chamber for introducing oxidizing reagent into said second chamber, an ultraviolet radiation source operatively coupled to said first and second chambers, said ultraviolet radiation source being disposed to simultaneously irradiate water in said first chamber and water and reagent in said second chamber, and second orifice means for conducting and directing water from said first to said second chamber, said second orifice means directing the water toward a mixing zone, wherein the water and the reagent are mixed in said second chamber and irradiated by ultraviolet radiation from said radiation source.

2. Apparatus in accordance with claim 1, and a source of microwave energy operatively coupled to said first chamber, whereby water in said first chamber is subjected to microwave radiation while being subjected to ultraviolet radiation.

3. Apparatus in accordance with claim 1, wherein said first orifice means is arranged to direct reagent toward the mixing zone.

4. Apparatus in accordance with claim 3, and a source of microwave energy operatively coupled to said first chamber, whereby water in said first chamber is subjected to microwave radiation while being subjected to ultraviolet radiation.

5. Apparatus in accordance with claim 1, wherein said mixing zone is a focal zone, said second orifice means providing a plurality of water streams directed from different directions toward said focal zone.

6. Apparatus in accordance with claim 5, and said first orifice means providing a plurality of reagent streams directed form different directions toward said focal zone.

7. Apparatus in accordance with claim 1, wherein said first chamber is cylindrical and has a longitudinal axis, and said water inlet port is transversely and obliquely oriented with respect to said longitudinal axis, whereby water in said first chamber is directed into a helical path.

8. Apparatus in accordance with claim 7, wherein said second orifice means comprises a ringjet, said ringjet providing a plurality of water streams into said second chamber in the direction of said focal zone.

9. Apparatus in accordance with claim 8, wherein said first orifice means is operatively associated with said ringjet, said first orifice means providing a plurality of reagent streams directed from different directions toward said focal zone.

10. Apparatus in accordance with claim 1, and a light conductor operatively coupled to said ultraviolet radiation source, said conductor extending through said first chamber and into operative communication with said second chamber, said ultraviolet radiation source comprising a lamp and light conductors operatively interconnecting said lamp and said conduit means.

11. Apparatus in accordance with claim 10, wherein said mixing zone is a focal zone, said second orifice means comprising a ringjet providing a plurality of water streams from different directions toward said focal zone.

12. Apparatus in accordance with claim 10, and a source of microwave radiation operatively coupled to said first chamber and juxtaposed to said water inlet port, whereby water in said first chamber is subjected to microwave radiation while being irradiated by ultraviolet radiation.

13. Apparatus in accordance with claim 12, wherein said mixing zone is a focal zone, said second orifice means comprising a ringjet providing a plurality of water streams from different directions toward said focal zone.

14. Apparatus in accordance with claim 13, wherein said conductor comprises quartz tube means, and a reflector in said first chamber for enhancing the distribution of ultraviolet radiation in said chamber.

15. Apparatus in accordance with claim 14, wherein said reflector has a quadratic surface.

16. Apparatus in accordance with claim 15, wherein said reflector has a sapphire coating.

17. For use in the treatment of water, an ionizing reactor comprising a cylindrical body having a longitudinal axis and first and second coaxial chambers; a water inlet port operatively associated with said first chamber and angularly offset from said longitudinal axis so that a water stream entering said first chamber from said inlet port assumes therein a helical path; a water outlet in fluid communication with said second chamber; light conducting means in light transmitting association with said first and second chambers; means associated with said second chamber for introducing into said second chamber a stream of oxidizing reagent, a source of ultraviolet radiation operatively coupled to said light conducting means so that the application of ultraviolet radiation to said light conducting means simultaneously irradiates water in said first chamber and water and reagent in said second chamber; a first orifice directing water from said first to said second chamber, said orifice providing a plurality of convergent water streams directed toward a focal zone, a second orifice operatively associated with said first orifice for injecting reagent into said second chamber toward said focal zone, whereby ultraviolet radiation transmitted to said second chamber irradiates water and reagent in said second chamber.

18. Reactor in accordance with claim 17, and a source of microwave energy operatively associated with said first chamber for subjecting water in said first chamber to microwave radiation.

\* \* \* \* \*